US010569241B1

(12) United States Patent
Wiederin

(10) Patent No.: US 10,569,241 B1
(45) Date of Patent: *Feb. 25, 2020

(54) SAMPLE INTRODUCTION SYSTEM WITH MIXING

(71) Applicant: Elemental Scientific, Inc., Omaha, NE (US)

(72) Inventor: Daniel R. Wiederin, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 139 days.

This patent is subject to a terminal disclaimer.

(21) Appl. No.: 15/838,673

(22) Filed: Dec. 12, 2017

Related U.S. Application Data

(63) Continuation of application No. 14/461,588, filed on Aug. 18, 2014, now Pat. No. 9,844,761, which is a continuation of application No. 13/868,300, filed on Apr. 23, 2013, now Pat. No. 8,806,966, which is a continuation of application No. 12/881,906, filed on Sep. 14, 2010, now Pat. No. 8,438,939.

(60) Provisional application No. 61/242,217, filed on Sep. 14, 2009.

(51) Int. Cl.
*B01F 13/02* (2006.01)
*H01J 49/04* (2006.01)
*H01J 49/10* (2006.01)
*G01N 1/22* (2006.01)

(52) U.S. Cl.
CPC ...... *B01F 13/0222* (2013.01); *B01F 13/0205* (2013.01); *G01N 1/22* (2013.01); *H01J 49/0445* (2013.01); *H01J 49/105* (2013.01); *B01F 2215/0037* (2013.01)

(58) Field of Classification Search
CPC .. G01N 2001/10; G01N 2001/14; G01N 1/38; G01N 1/002; G01N 35/1095; G01N 1/22; B01F 13/0222; B01F 13/0205; B01F 2215/0037; H01J 49/0445; H01J 49/105
See application file for complete search history.

(56) References Cited

U.S. PATENT DOCUMENTS

| | | | |
|---|---|---|---|
| 3,719,086 A | 3/1973 | Bannister et al. |
| 3,726,144 A | 4/1973 | Klein |
| 4,000,974 A | 1/1977 | Acord |
| 4,054,415 A | 10/1977 | Seligson et al. |
| 4,148,610 A | 4/1979 | Miller, Jr. et al. |
| 4,362,401 A | 11/1982 | Smith, Jr. et al. |
| 4,811,611 A | 3/1989 | Uffenheimer |
| 4,930,898 A | 6/1990 | Miller-Ihli |
| 5,111,703 A | 5/1992 | Allen |

(Continued)

FOREIGN PATENT DOCUMENTS

| | | |
|---|---|---|
| CA | 2274887 A1 | 1/2000 |
| EP | 0490592 A1 | 6/1992 |
| JP | 2007047027 A | 2/2007 |

*Primary Examiner* — Robert R Raevis
(74) *Attorney, Agent, or Firm* — Kevin E. West; Advent, LLP

(57) ABSTRACT

A sample introduction system provides mixing of a sample and a diluent within the container via gas injection. In one or more implementations, the sample introduction system causes a probe of an autosampler to be inserted into a container containing a sample and a diluent so that an end of the probe is submerged beneath a surface of the diluent and the sample. Gas is then injected through the probe to mix the sample and the diluent within the container. An aliquot of the mixed sample and diluent is then withdrawn through the probe.

13 Claims, 8 Drawing Sheets

(56) References Cited

U.S. PATENT DOCUMENTS

| | | |
|---|---|---|
| 5,163,582 A | 11/1992 | Godolphin et al. |
| 5,174,966 A | 12/1992 | Durand et al. |
| 5,343,770 A | 9/1994 | Seidoh et al. |
| 5,389,339 A | 2/1995 | Petschek et al. |
| 5,506,142 A | 4/1996 | Mahaffey et al. |
| 6,040,186 A | 3/2000 | Lewis et al. |
| 6,063,635 A | 5/2000 | Ohta et al. |
| 6,143,573 A | 11/2000 | Rao et al. |
| 6,872,362 B2 | 3/2005 | Schmidt et al. |
| 7,205,158 B2 | 4/2007 | Pankratz et al. |
| 2002/0086431 A1 | 7/2002 | Markham et al. |
| 2005/0079079 A1 | 4/2005 | Wahlin et al. |

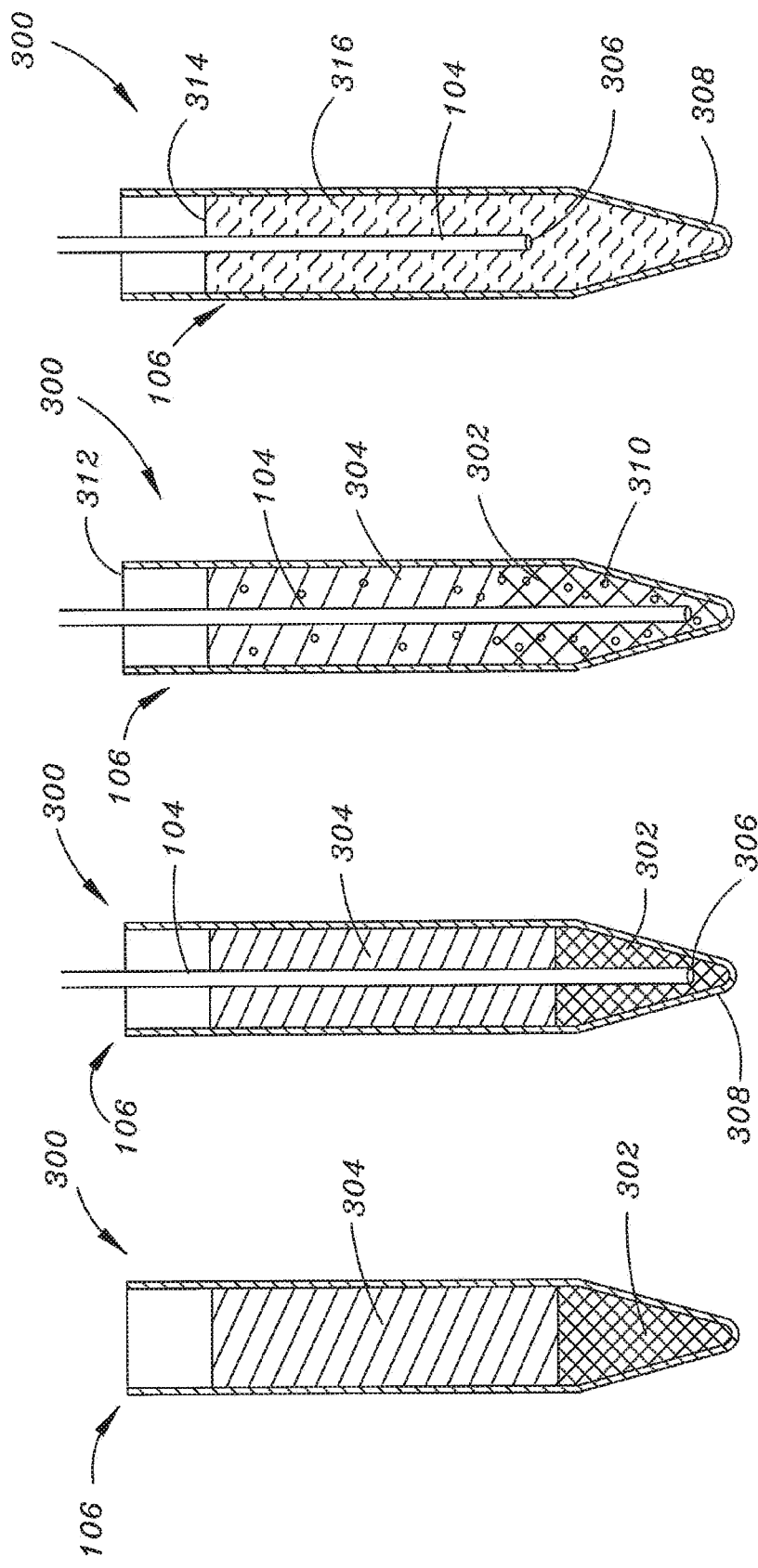

SAMPLE INTRODUCTION SYSTEM WITH MIXING

CROSS-REFERENCE TO RELATED APPLICATIONS

The present application is a continuation under 35 U.S.C. § 120 of U.S. patent application Ser. No. 14/461,588, filed Aug. 18, 2014, and titled "SAMPLE INTRODUCTION SYSTEM WITH MIXING," which itself is a continuation under 35 U.S.C. § 120 of U.S. patent application Ser. No. 13/868,300, filed Apr. 23, 2013, and titled "SAMPLE INTRODUCTION SYSTEM WITH MIXING," and U.S. patent application Ser. No. 12/881,906, filed Sep. 14, 2010, and titled "SAMPLE INTRODUCTION SYSTEM WITH MIXING," which itself claims priority under 35 U.S.C. § 119(e) of U.S. Provisional Application Ser. No. 61/242,217, filed Sep. 14, 2009, and titled "SAMPLE INTRODUCTION SYSTEM WITH MIXING." U.S. patent application Ser. Nos. 14/461,588; 13/868,300; and 12/881,906 and U.S. Provisional Application Ser. No. 61/242,217 are herein incorporated by reference in their entireties.

BACKGROUND

Inductively coupled plasma (ICP) mass spectroscopy is an analysis technique commonly used for the determination of trace element concentrations and isotope ratios in liquid samples. ICP mass spectroscopy employs electromagnetically generated partially ionized argon plasma which reaches a temperature of approximately 7000K. When a sample is introduced to the plasma, the high temperature causes sample atoms to become ionized or emit light. Since each chemical element produces a characteristic mass or emission spectrum, measuring said spectra allows the determination of the elemental composition of the original sample.

Sample introduction systems may be employed to introduce the liquid samples into the ICP mass spectroscopy instrumentation (e.g., an inductively coupled plasma mass spectrometer (ICP/ICPMS), an inductively coupled plasma atomic emission spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP mass spectrometry instrumentation. The aerosol is then sorted in a spray chamber to remove the larger aerosol particles. Upon leaving the spray chamber, the aerosol is introduced to the ICPMS or ICPAES instruments for analysis. Often, the sample introduction is automated to allow a large number of samples to be introduced into the ICP mass spectroscopy instrumentation in an efficient manner.

SUMMARY

A sample introduction system is described that provides mixing of a sample and a diluent within the container via gas injection. In one or more implementations, the sample introduction system causes a probe, such as the probe of an autosampler, to be inserted into a container containing a sample and a diluent so that an end of the probe is submerged beneath a surface of the diluent and the sample. Gas is then injected through the probe to mix the sample and the diluent within the container. An aliquot of the mixed sample and diluent is then withdrawn through the probe.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

FIGS. 3A, 3B, 3C, and 3D are illustrations depicting an example container containing a sample and diluent during mixing of the sample and diluent using gas injection and withdrawal of a aliquot of mixed sample and diluent in accordance with the procedure of FIG. 2.

DETAILED DESCRIPTION

Overview

ICP mass spectroscopy may be used in the analysis of oil samples. For example, ICP mass spectroscopy analysis of motor oil is often used by enterprises that maintain a large number of vehicles. Parts that wear in an engine will deposit trace metals in the engine's oil. Analysis of the used motor oil of an engine provides information about how the engine is operating by identifying worn parts within the engine. In addition, ICP mass spectrometry analysis can determine the amounts of the original oil additives remain within the oil after a period of use, thus providing an indication of the amount service life the oil has remaining.

When samples of oil are analyzed, a diluent such as kerosene may be added to reduce the viscosity of the oil allowing an aliquot of the sample to be withdrawn for analysis. Generally, the oil sample and the diluent are provided in a container in an unmixed state. Consequently, prior to taking an aliquot of the sample for ICP mass spectrometry analysis, the sample and diluent are first mixed.

Accordingly, a sample introduction system is described that provides mixing of a sample and a diluent within the container via gas injection. The sample introduction system includes an auto sampler configured to insert a probe into a container holding a sample and a diluent so that an end of the probe is submerged beneath the surface of the sample and the diluent. A valve assembly is configured to cause gas to be injected into the container through the probe to mix the sample and the diluent within the container via bubbling. For example, in one or more implementations, the gas is injected in a series of short bursts to mix the sample and diluent. The valve assembly may then be configured to cause a vacuum to be applied to the probe to withdraw an aliquot of the mixed sample and diluent through the probe into a sample loop. By mixing the oil with the same probe that withdraws the aliquot through gas injection, the throughput of the sample introduction system is increased in comparison with sample introduction systems that use separate mixing apparatus. For example, in one implementation, the analysis time per sample of the sample introduction system may be reduced to less than about 24 seconds. Additionally, in implementations where a screened probe is used, the injection of gas through the probe may cause fibrous contaminants to be removed from the screen.

In the following discussion, an example environment is first described. Example functionality is then described that may be implemented by the sample introduction system in the exemplary environment, as well as in other environments without departing from the spirit and scope thereof.

Example Environment

Figure 1A:
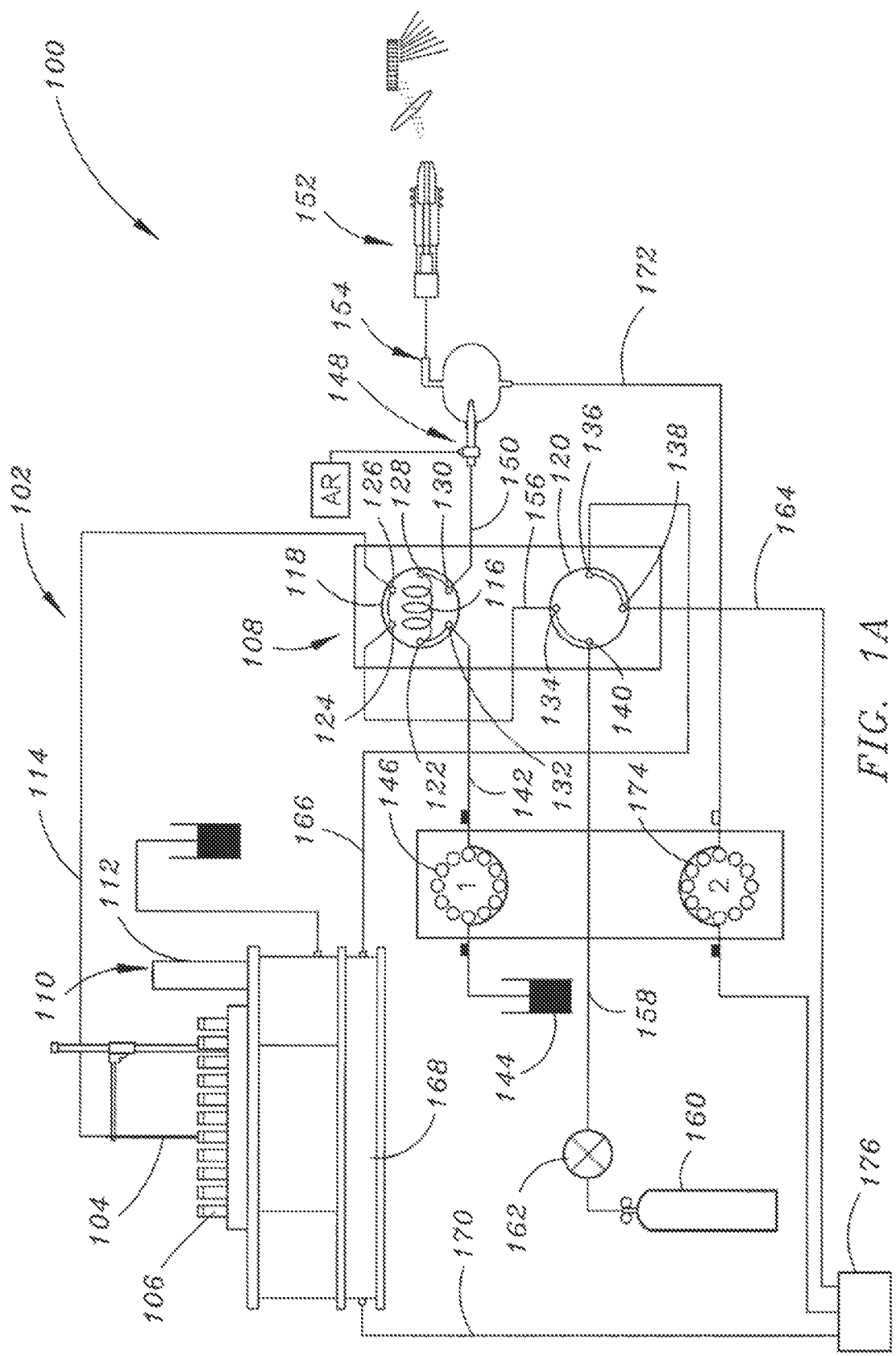
FIGS. 1A, 1B, and 1C are illustrations of an environment in an example implementation that employs a sample introduction system that provides mixing using gas injection.
Figure 1B:
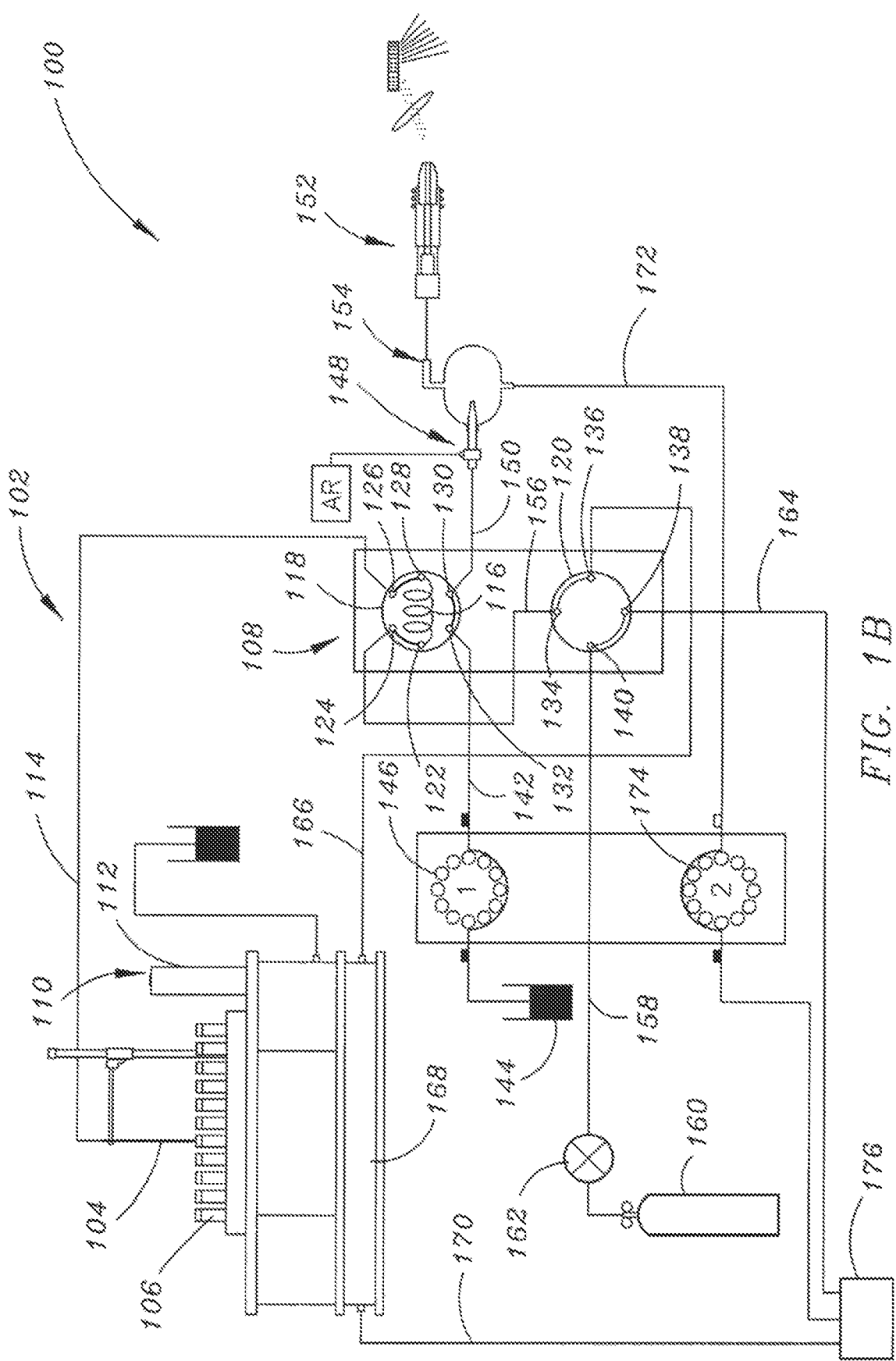
Figure 1C:
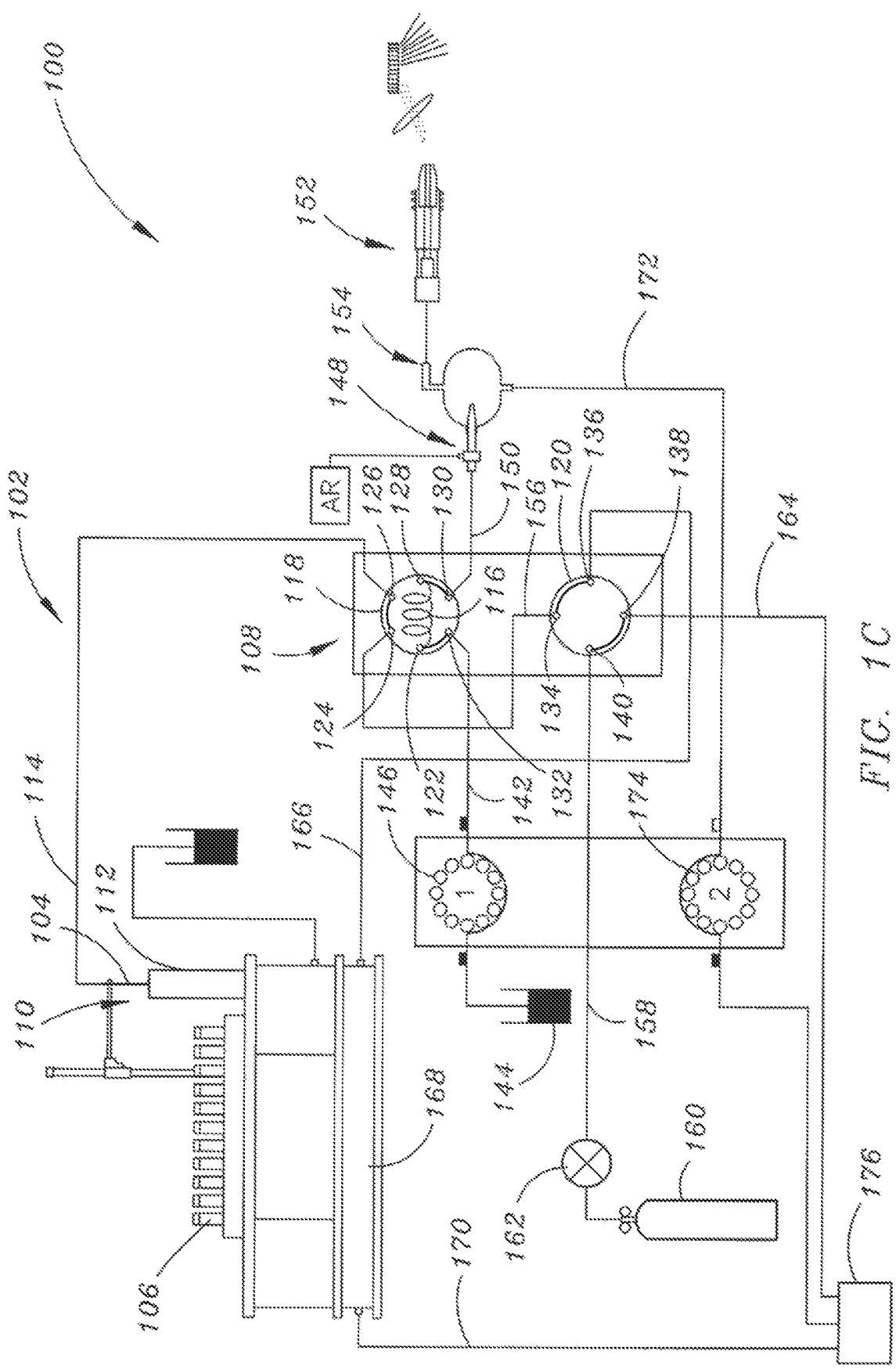

FIGS. 1A, 1B, and 1C illustrate an environment 100 in an example implementation that employs a sample introduction system 102 which provides mixing of samples with diluent using gas injection. As shown, the sample introduction system 102 includes a probe 104 that comprises a hollow tubular structure configured to be inserted into a container 106 that holds a sample to which a liquid diluent has been added. In the implementation illustrated, the probe 104 includes a single internal passageway through which gas is injected into the sample and diluent, and through which the aliquot of the mixed sample and diluent is withdrawn. In embodiments, the probe 104 may include an integral support formed of a generally rigid material such as carbon fiber, stainless steel, polyaryletheretherketone (PEEK), polyetherimide (PEI), or the like, encapsulated with polytetrafluoroethylene (PTFE). However, other probe structures are possible. Example probes 104 are shown in greater detail in FIGS. 3B, 3C, 3D, 4A, 4B, and 6.

The probe 104 may be coupled to an autosampler 110 that moves the probe 104 among a plurality of containers 106 in a tray or rack in a predetermined order. The autosampler 110 inserts the probe 104 into each of the containers 106 so that an aliquot of the diluted sample may be withdrawn for analysis. After the probe 104 is withdrawn from a container 106, the autosampler 110 may rinse the probe 104 by inserting the probe 104 into a rinse station 112 containing a suitable rinse fluid, such as the diluent, or the like.

The autosampler 110 may provide functionality to control operation of other components of the sample introduction system 102. Control of components of the sample introduction system 102 may also be provided by a separate control module, a general purpose computer, or the like. In the implementation shown, the autosampler 110 may be configured in accordance with one or both of U.S. Pat. Nos. 7,201,072 and 7,469,606, which are herein incorporated by reference in their entireties. However, autosamplers 110 having other configurations may be employed.

The sample introduction system 102 further includes a valve assembly 108 coupled to the probe 104 via a capillary 114. The valve assembly 108 is configured to cause gas to be injected into a container 106 in which the probe 104 has been inserted, through the capillary 114 and probe 104 to mix the sample and the diluent within the container 106 via bubbling. The valve assembly 108 then causes a vacuum to be applied to the probe 104 via the capillary 114 to withdraw an aliquot of the mixed sample and diluent through the probe 104 and capillary 114 into a sample loop 116, which temporarily holds the aliquot.

In the example implementation illustrated, the valve assembly 108 includes a first valve 118 and a second valve 120. The first valve 118 comprises a six port valve that includes a first port 122, a second port 124, a third port 126, a fourth port 128, a fifth port 130, and a sixth port 132, while the second valve 120 comprises a four port valve that includes a first port 134, a second port 136, a third port 138, and a fourth port 140.

The first valve 118 may be actuated between a first state, shown in FIGS. 1A and 1B and a second state, shown in FIG. 1C. When the first valve 118 is actuated to its first state, the first valve 118 connects the first port 122 with the sixth port 132, the second port 124 with the third port 126, and the fourth port 128 with the fifth port 130 to allow flow between the respective pairs of connected ports. Conversely, when the first valve 118 is actuated to its second state, the first valve 118 instead connects the first port 122 with the second port 124, the third port 126 with the fourth port 128, and the fifth port 130 with the sixth port 132 to allow flow between the respective pairs of connected ports.

The second valve 120 may similarly be actuated between a first state, shown in FIGS. 1A and 1C, and a second state, shown in FIG. 1B. When the second valve 120 is actuated to its first state, the second valve 120 connects the first port 134 with the fourth port 140 and the second port 136 with the third port 138 to allow flow between the respective pairs of connected ports. Conversely, when the second valve 120 is actuated to its second state, the second valve 120 instead connect the first port 134 with the second port 136 and the third port 138 with the fourth port 140 to allow flow between the respective pairs of connected ports.

As shown, the sample loop 116 is coupled to, and extends between, the first port 122 and the fourth port 128 of the first valve 118. The sample loop 116 is comprised of a loop of tubing having a length sufficient to hold at least a portion of the aliquot of mixed sample and diluent withdrawn from a container 106. In embodiments, the sample loop 116 is formed of a suitable material, such as PTFE, or the like. However, it is contemplated that the sample loop 116 may have other configurations. For example, the sample loop 116 may include a column, or like component, that is configured to further process (e.g., filter) the sample and diluent.

A diluent carrier is furnished via a line 142 coupled to the sixth port 132 of the first valve 118. The diluent carrier may be supplied from a reservoir 144 of diluent by a pump (a peristaltic pump 146 is illustrated) at a predetermined flow rate. For example, in embodiments where the sample introduction system 102 is used in the analysis of oil samples, the diluent carrier may be kerosene supplied at a flow rate of at least about 2 mL/min. However, the use of other flow rates is contemplated.

In the example implementation shown, a nebulizer 148 is interconnected with the valve assembly 108 via a line 150 coupled to the fifth port 130 of the first valve 118. As noted, the nebulizer 148 converts mixed sample and diluent received from the sample loop 116 into a polydisperse aerosol suitable for ionization in plasma by the ICP mass spectroscopy instrumentation 152 (e.g., ICPMS, ICPAES, or the like). The aerosol is then sorted in a spray chamber 154 to remove larger aerosol particles. Upon leaving the spray chamber 154, the aerosol is introduced to the ICP mass spectroscopy instrumentation 152 for analysis.

The capillary 114 of the probe 104 is coupled to the third port 126 of the first valve 118. In embodiments, the capillary 114 comprises a length of tubing formed of a suitable material, such as PTFE, or the like, which is sufficiently flexible to allow movement of the probe 104 by the autosampler 110.

A second port 124 of the first valve 118 is coupled to the first port 134 of the second valve 120 via line 156. A supply of gas is furnished via a line 158 coupled to the fourth port 140 of the second valve 120. The gas supplied via line 158 may be any gas suitable for use with the sample and diluent. For example, in embodiments where the sample introduction system 102 is used in the analysis of oil samples, the gas supplied may be Argon (Ar) or Nitrogen ($N_2$). As shown, the gas may be supplied from a source 160 such as a pressurized tank, or the like. A regulator 162 regulates the pressure of the gas. For example, in embodiments where the sample introduction system 102 is used in the analysis of oil samples, the pressure may be regulated to about 0.25 bar by the regulator 162. However, regulation of the pressure of the gas supplied to line 158 to other pressures is contemplated.

A vent line 164 may be connected to the third port 138 of the second valve 120. In some embodiments, the vent line 164 may vent unused gas to atmosphere. In other embodiments, the vent line 164 may be coupled to a gas collection system to collect unused gas, for example, to be recycled. In further embodiments, vent line 164 may be capped so that unused gas does not vent.

A vacuum is supplied to the second port 136 of the second valve 120 via line 166. In embodiments, the vacuum may be supplied by a vacuum pump 168 coupled to line 166. In the implementation shown, the vacuum pump 168 is configured as a component of the autosampler 110. However, it is contemplated that the vacuum pump 168 may also be a separate component of the sample introduction system 102, may be combined with another component of the sample introduction system 102 such as a control module, or the like.

A first waste line 170 may be coupled to the vacuum pump 168 (e.g., the autosampler 110). Similarly, a second waste line 172 may be coupled to the spray chamber 154. The waste lines 170, 172 receive excess sample and/or diluent from the autosampler 110 and/or the spray chamber 154, respectively. In embodiments, a waste receptacle 176 may be coupled to the waste lines 170, 172 to receive the excess sample and/or diluent for disposal. A pump (a peristaltic pump 174 is shown) may be provided to draw the excess sample/diluent through the second waste line 172 from the spray chamber 154.

In embodiments, lines 142, 150, 156, 158, 164, 166, 170, 172 may comprise lengths of flexible tubing formed of a suitable material, such as PTFE, or the like. However, other configurations are possible.

FIGS. 1A, 1B, and 1C illustrate an example implementation of the sample introduction system 102 which provides mixing of samples with diluent using gas injection. However, it is contemplated that other implementations are possible. For example, a sample introduction system 102 in another implementation may employ a valve assembly that utilizes a single multiple-port valve, a valve assembly that utilizes three or more valves, and so on. Similarly, a sample introduction system 102 in another implementation may employ a separate control module in addition to the autosampler 110.

Example Procedures

Figure 2:
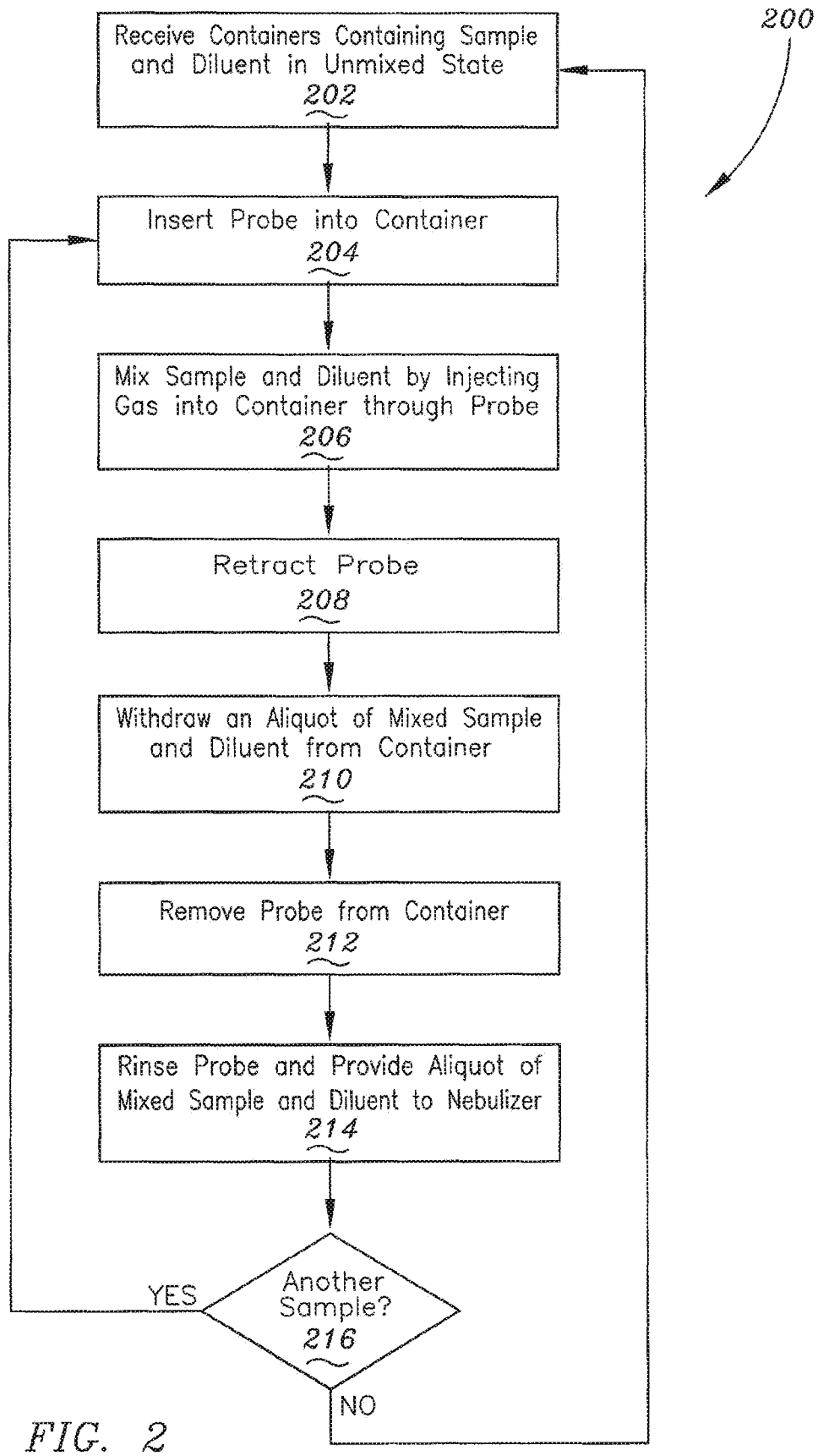
FIG. 2 is a flow diagram illustrating a procedure that may be employed by a sample introduction system such as the sample introduction system of the environment shown in FIGS. 1A, 1B, and 1C to mix a sample and diluent using gas injection and withdraw an aliquot of the mixed sample and diluent.
Figure 4B:
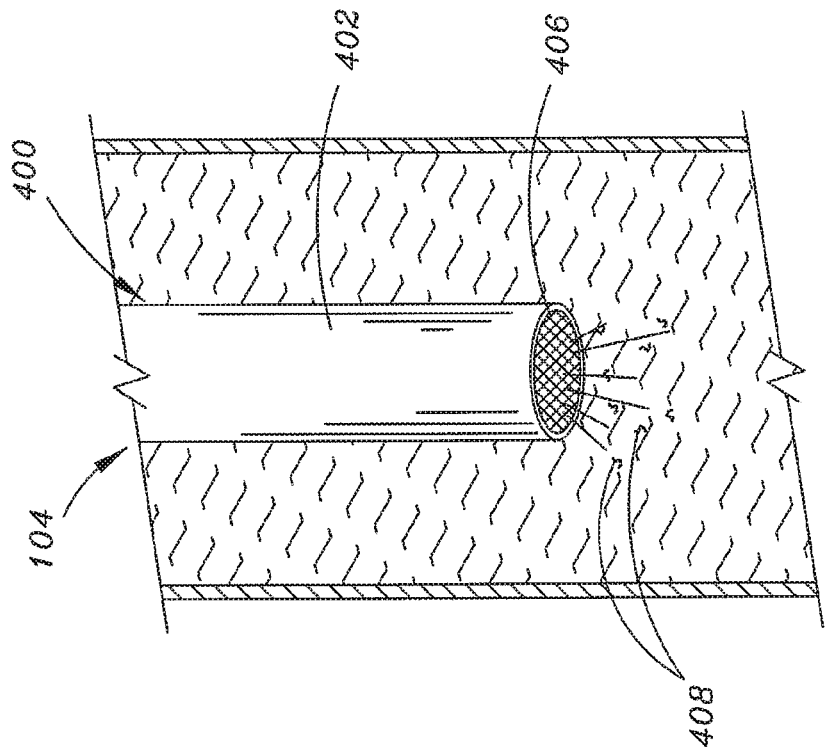
FIGS. 4A and 4B are illustrations depicting cleaning of the screen of a screened probe using gas injection.
Figure 4A:
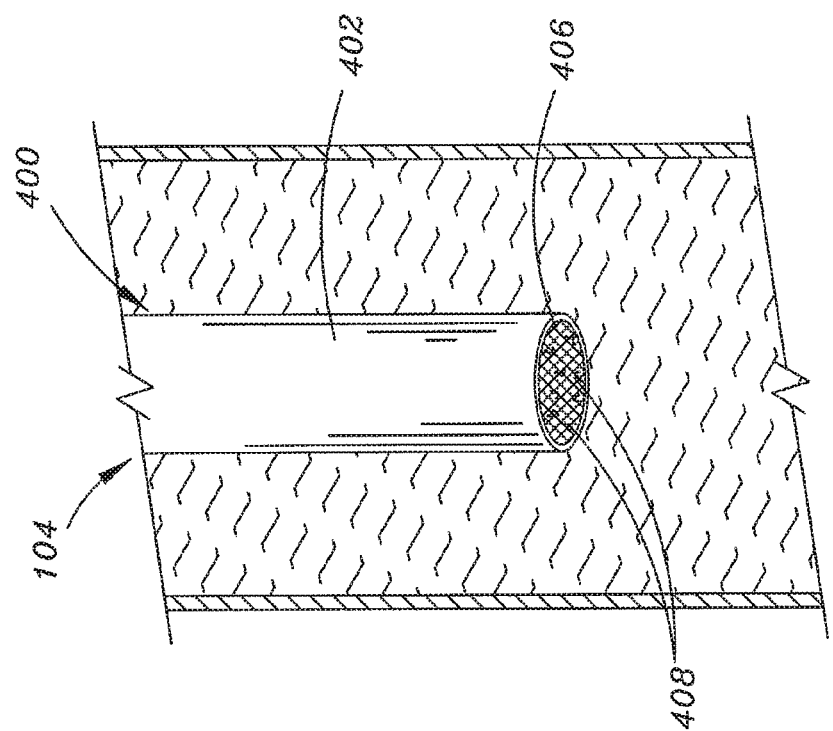

FIG. 2 illustrates an example procedure 200 suitable for use by the sample introduction system 102 in the environment 100 of FIGS. 1A, 1B, and 1C to mix a sample and diluent within a container 106 using gas injection and withdraw an aliquot of the mixed sample and diluent for analysis. As shown in FIG. 2, one or more containers that contain a sample and a diluent in an unmixed state are received for analysis (Block 202). For instance, as shown in FIGS. 1A, 1B, and 1C, containers 106 containing various samples to which a diluent has been added may be received in a sample tray of the autosampler 110 in preparation for analysis of the samples by the ICP mass spectroscopy instrumentation 152.

FIGS. 3A, 3B, 3C and 3D illustrate an example container 106, in this instance a sample vial 300, that contains a sample 302 and diluent 304. FIG. 3A shows the sample vial 300 while the sample 302 and diluent 304 are in an unmixed state. Because the sample 302 is normally denser than the diluent 304, the sample 302 may tend to settle to the bottom surface 308 of the sample vial 300, while the diluent 304 tends to float on top of the sample 302. For example, in embodiments where the sample introduction system 102 is used in the analysis of oil samples, the sample 302 may comprise used engine oil, while the diluent 304 is comprised of kerosene which, being less dense tends to float on the surface of the oil. In one or more such embodiments in which the oil is diluted by a factor of ten (e.g., a 10× dilution), the sample vial 300 may be sized to contain approximately 1 ml of oil diluted with 9 ml of kerosene.

Referring again to FIG. 2, the probe 104 is then inserted into a first of the containers 106 (Block 204). In embodiments, the sample introduction system 102 may cause the autosampler 110 to insert the probe 104 into the container 106 until the end of the probe 104 is in a position proximal to a bottom surface of the container 106.

FIG. 3B illustrates the sample vial 300 containing a sample 302 and diluent 304 shown in FIG. 3A, in which a probe 104 has been inserted. As shown, the probe 104 is inserted into the sample vial 300 until the end 306 of the probe 104 is in a position proximal to the bottom surface 308 of the container 106. Thus, the end 306 of the probe 104 is generally submerged within the sample 302.

The sample and diluent are next mixed (Block 206) by injecting gas into the container 106 through the probe 104 to cause bubbling of the sample and diluent. For example, as shown in FIG. 1A, the first valve 118 is actuated to its first state so that the second port 124 of the first valve 118 is connected with the third port 126 to couple the capillary 114 to line 156. The second valve 120 is also actuated to its first state so that the first port 134 of the second valve 120 is connected with the fourth port 140 to couple line 156 with line 158. In this manner, gas is supplied to the probe 104 from the gas source 160 for injection into the container 106.

FIG. 3C illustrates injection of a gas 310 into the sample vial 300 by the probe 104 to mix the sample 302 and diluent 304 via bubbling. In one or more embodiments, gas may be injected in a series of short bursts to mix the sample 302 and diluent 304. Use of short burst of gas provides efficient mixing of the sample 302 and diluent 304, while preventing the sample 302 and diluent 304 from bubbling over the top 312 of the sample vial 300. It is contemplated the length of each burst and/or the period separating successive bursts may be constant or may vary (e.g., increase or decrease, be randomly selected, and so on). Thus, the number and length of the bursts, and the period separating the bursts may be selected to maximize the efficiency of mixing of the sample 302 and diluent 304. For instance, in embodiments where the sample introduction system 102 is used in the analysis of oil samples, gas 310 may be injected in three or more bursts having durations of about 0.1 seconds each, separated by periods between successive bursts of about 0.1 seconds in duration.

The probe 104 may then be retracted (Block 208) by the autosampler 110. For example, as shown in FIG. 3D, the probe 104 may be withdrawn from the position shown in FIG. 3C, wherein the end 306 of the probe 104 is proximal to the bottom surface 308 of the sample vial 300 following injection of the gas 310 and mixing of the sample 302 and diluent 304. The probe 104 may be withdrawn until the end 306 of the probe 104 is spaced away from the bottom surface 308 but is held beneath the surface 314 of the mixed sample and diluent 316.

An aliquot of the mixed sample and diluent is then withdrawn from the container 106 (Block 210). For example, as shown in FIG. 1B, after injection of the gas, the first valve 118 is actuated to its second state so that the first port 122 of the first valve 118 is connected with the second port 124 and the third port 126 is connected with the fourth port 128 to couple the sample loop 116 between the capillary 114 and line 156. The second valve 120 is also actuated to its second state so that the first port 134 of the second valve 120 is connected with the second port 136 to couple line 156 with line 166. In this manner, a vacuum is applied to the probe 104 to draw the mixed sample and diluent through the probe 104 and capillary 114 into the sample loop 116. FIG. 3D illustrates the position of the probe 104 within the sample vial 300 during withdrawal of the aliquot of the mixed sample and diluent 316.

While the first and second valves 118, 120 are actuated to their second states as shown in FIG. 1B, the fifth port 130 of the first valve 118 is coupled to the sixth port 132 to couple line 142 to line 150 so that carrier diluent may be supplied to the nebulizer 148 to rinse the injector of the nebulizer 148. Moreover, the third port 138 of the second valve 120 is connected to the fourth port 140 so that excess mixed sample and diluent 316 may be ported to the waste receptacle 176 via vent line 164.

Referring again to FIG. 2, the probe 104 is then removed from the container 106 (Block 212) by the autosampler 110 and rinsed (Block 214). In the implementation illustrated in FIGS. 1A, 1B, and 1C, the autosampler 110 may cause the probe 104 to be moved to and inserted within the rinse station 112. A rinse fluid (e.g., the diluent) may then be drawn through the probe 104. Simultaneously, the aliquot of mixed sample and diluent that was drawn into the sample loop 116 may be provided to the nebulizer 148 for conversion into a polydisperse aerosol suitable for ionization in plasma by the ICP mass spectroscopy instrumentation 152.

As shown in FIG. 1C, the first valve 118 is actuated to its first state so that the second port 124 of the first valve 118 is connected with the third port 126 to couple the capillary 114 to line 156. The second valve 120 is actuated to its second state so that the first port 134 of the second valve 120 is connected with the second port 136 to couple line 156 with line 166. In this manner, a vacuum is applied to the capillary 114 to draw rinse fluid through the probe 104, the capillary 114, first valve 118, line 156, second valve 120, and line 166. The rinse fluid is then transported to the waste receptacle 176 via waste line 170.

The first port 122 of the first valve 118 is also connected with the sixth port 132, while the fourth port 128 of the first valve 118 is connected with the fifth port 130 to couple line 142 to line 150. In this manner, diluent carrier supplied from the reservoir 144 of diluent by peristaltic pump 146 may be used to advance the aliquot of mixed sample and diluent that was drawn into the sample loop 116 into the nebulizer 148.

If additional samples are to be analyzed ("Yes" from Decision Block 216), the probe 104 is inserted into the next container 106 containing a sample to be analyzed, and the procedure 200 (Blocks 204-216) is repeated. When no more samples remain to be analyzed ("No" from Decision Block 216), the procedure 200 may be halted or paused until additional containers 106 are received for analysis (Block 202).

It is contemplated that, in one or more embodiments, the probe 104 may be rinsed (Block 214) prior to initial insertion of the probe 104 into the first of the containers 106 (Block 204) as described above. Further, gas may be injected through the probe 104 while the probe 104 is rinsed (Block 214). For example, in some embodiments, the probe 104 may employ a screen member (e.g., a screen, a filter, or the like) to filter fibrous contaminants from the sample and diluent so that the contaminants do not enter the probe 104. The injection of gas through the probe 104 may have the effect of causing the fibrous contaminants to be removed from the screen during rinsing and/or during mixing of the sample and diluent.

Injection of gas by the sample introduction system 102 may be accomplished by actuating the first and second valves 118, 120 to their first state while the probe 104 is inserted within the rinse station 112 by the autosampler 110. As shown in FIG. 1A, the second port 124 of the first valve 118 is thus connected with the third port 126 to couple the capillary 114 to line 156, while the first port 134 of the second valve 120 is connected with the fourth port 140 to couple line 156 with line 158, so that gas is supplied to the probe 104 from the gas source 160. The second valve 120 may be actuated to its first state either before or after injection of the gas to draw the rinse solution through the probe 104 as described above.

FIGS. 4A and 4B illustrate an example probe 104, in this instance a screened probe 400, that is cleaned using gas injection in accordance with the present disclosure. As shown, the probe 400 comprises a hollow tubular structure 402 having an end that includes a screen member 406. As shown in FIG. 4A, fibrous contaminants 408 filtered by the screen member 406 may tend to collect on the screen member 406, possibly reducing the flow of sample and diluent into the probe 400. As shown in FIG. 4B, the injection of gas through the probe 400 may dislodge at least some of the fibrous contaminants 408 from the screen member 406 into the rinse fluid during rinsing and/or into the sample and diluent during mixing.

FIG. 5 illustrates a procedure 500 in an example implementation that is suitable for use by the sample introduction system 102 in the environment 100 of FIGS. 1A, 1B, and 1C to add a diluent to a sample. In the implementation illustrated, the probe 104 is first rinsed (Block 502) to avoid contamination of the sample. For example, as shown in FIG. 1C, the autosampler 110 may cause the probe 104 to be moved to and inserted within the rinse station 112. The first valve 118 is actuated to its first state so that the second port 124 of the first valve 118 is connected with the third port 126 to couple the capillary 114 to line 156. The second valve 120 is actuated to its second state so that the first port 134 of the second valve 120 is connected with the second port 136 to couple line 156 with line 166. In this manner, a vacuum is applied to capillary 114 to draw rinse fluid through the probe 104, the capillary 114, first valve 118, line 156, second valve 120, and line 166. The rinse fluid is then transported to the waste receptacle 176 via waste line 170.

Gas may be injected through the probe 104 while the probe 104 is rinsed (Block 502). As shown in FIG. 1A, injection of gas by the sample introduction system 102 may be accomplished by actuating the first and second valves 118, 120 to their first state while the probe 104 is inserted within the rinse station 112 by the autosampler 110. The second port 124 of the first valve 118 is thus connected with the third port 126 to couple the capillary 114 to line 156, while the first port 134 of the second valve 120 is connected with the fourth port 140 to couple line 156 with line 158 so that gas is supplied to the probe 104 from the gas source 160. The second valve 120 may be actuated to its first state either before or after injection of the gas to draw the rinse solution through the probe 104 as described above.

Diluent may then be taken up into the probe 104 and/or the capillary 114 (Block 504). The autosampler 110 may cause the probe 104 to be inserted into a supply of diluent. The first valve 118 is actuated to its first state so that the second port 124 of the first valve 118 is connected with the third port 126 to couple the capillary 114 to line 156. The second valve 120 is actuated to its second state so that the first port 134 of the second valve 120 is connected with the second port 136 to couple line 156 with line 166. In this manner, a vacuum is applied to capillary 114 to draw the diluent into the probe 104 and capillary 114.

Next, a segmentation bubble may be taken up by the probe 104 (Block 506). For example, the autosampler 110 may cause the probe 104 to be removed from the supply of diluent. The first valve 118 is again actuated to its second state, while the second valve 120 is actuated to its second state so that the vacuum is briefly applied to the capillary 114 to draw atmospheric gas (e.g., air) into the probe 104 to form the segmentation bubble.

The sample is then taken up by the probe 104 (Block 508). For example, the autosampler 110 may cause the probe 104 to be moved to and inserted within a container 106 that contains an undiluted sample. The first valve 118 is again actuated to its second state, while the second valve 120 is actuated to its second state so that a vacuum is applied to the capillary 114 to draw the sample into the probe 104. It is contemplated that the segmentation bubble may be taken up by the probe as the autosampler 110 moves the probe from the supply of diluent to the container 106 that contains the sample to be taken up by the probe 104.

A second bubble may then be taken up by the probe 104 (Block 510) behind the sample. For example, the autosampler 110 may cause the probe 104 to be removed from the container containing the sample. The first valve 118 is again actuated to its second state, while the second valve 120 is actuated to its second state so that a vacuum is briefly applied to the capillary 114 to draw atmospheric gas (e.g., air) into the probe 104 to form the second bubble.

The sample and diluent are then expelled into a mixing container 106 (Block 512). For example, the autosampler 110 may cause the probe 104 to be moved to and inserted within an empty container 106. The first and second valves 118, 120 may then be actuated to their first state as shown in FIG. 1A. Thus, the second port 124 of the first valve 118 is connected with the third port 126 to couple the capillary 114 to line 156, while the first port 134 of the second valve 120 is connected with the fourth port 140 to couple line 156 with line 158 so that gas is supplied to the capillary 114 from the gas source 160. The gas causes the sample and diluent to be expelled from the capillary 114 and probe 104 into the empty container 106. It is contemplated that the second bubble may be taken up by the probe 104 as the autosampler 110 moves the probe 104 from the container 106 that contains the sample to the mixing container 106.

Figure 6:
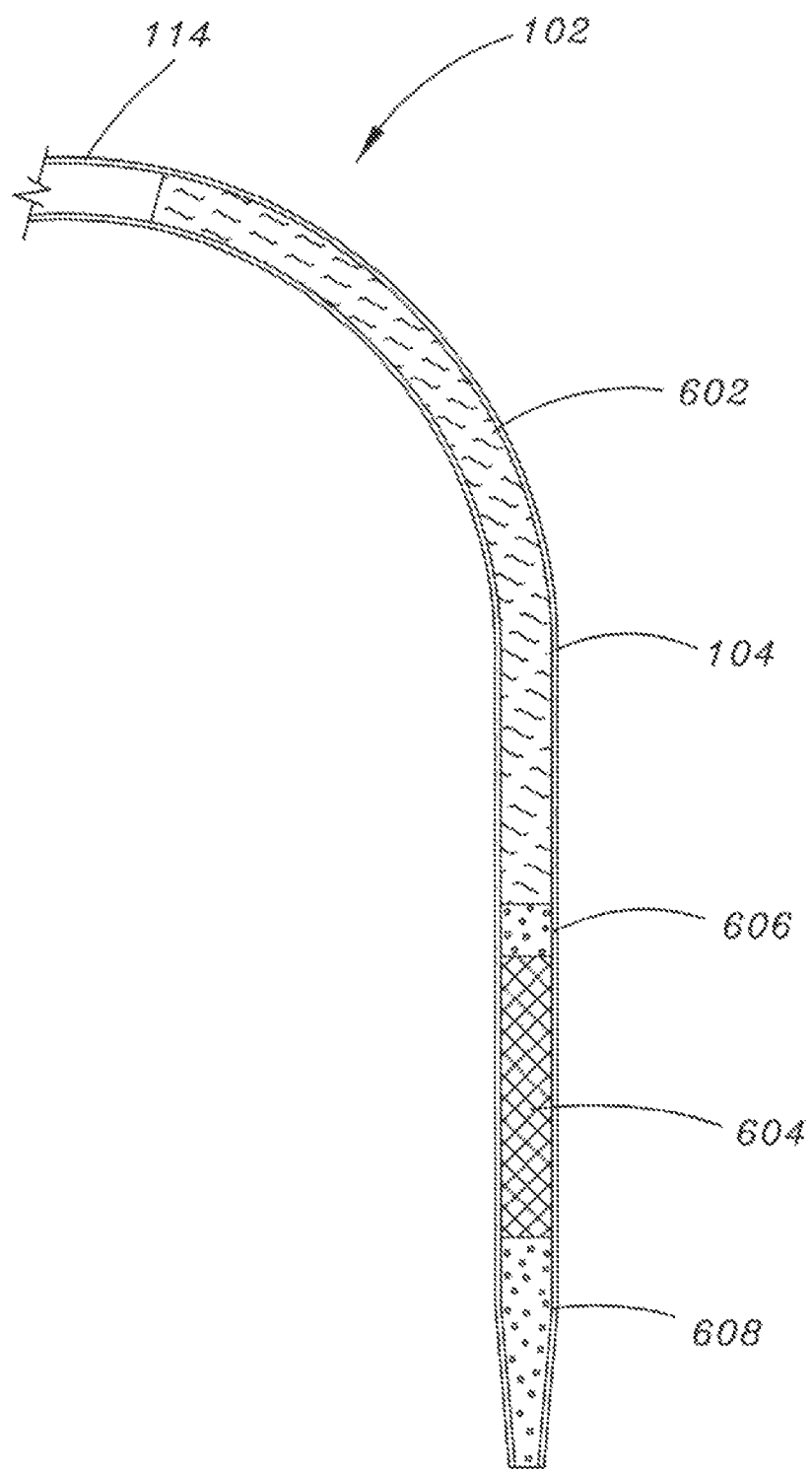
FIG. 6 is an illustration depicting the addition of a diluent to a sample in accordance with the procedure of FIG. 5.

FIG. 6 depicts the probe 104 and capillary 114 of the sample introduction system 102 after taking up the diluent 602 and sample 604. Segmentation bubble 606 separates the diluent 602 and the sample 604, while second bubble 608 prevents leakage of the sample 604 from the probe 104. In one or more embodiments, about 9 mL of diluent 602 and about 1 mL of sample are taken up by the probe 104. However, it is contemplated that amounts of diluent 602 and sample 604 may also be taken up by the probe 104.

Figure 5:
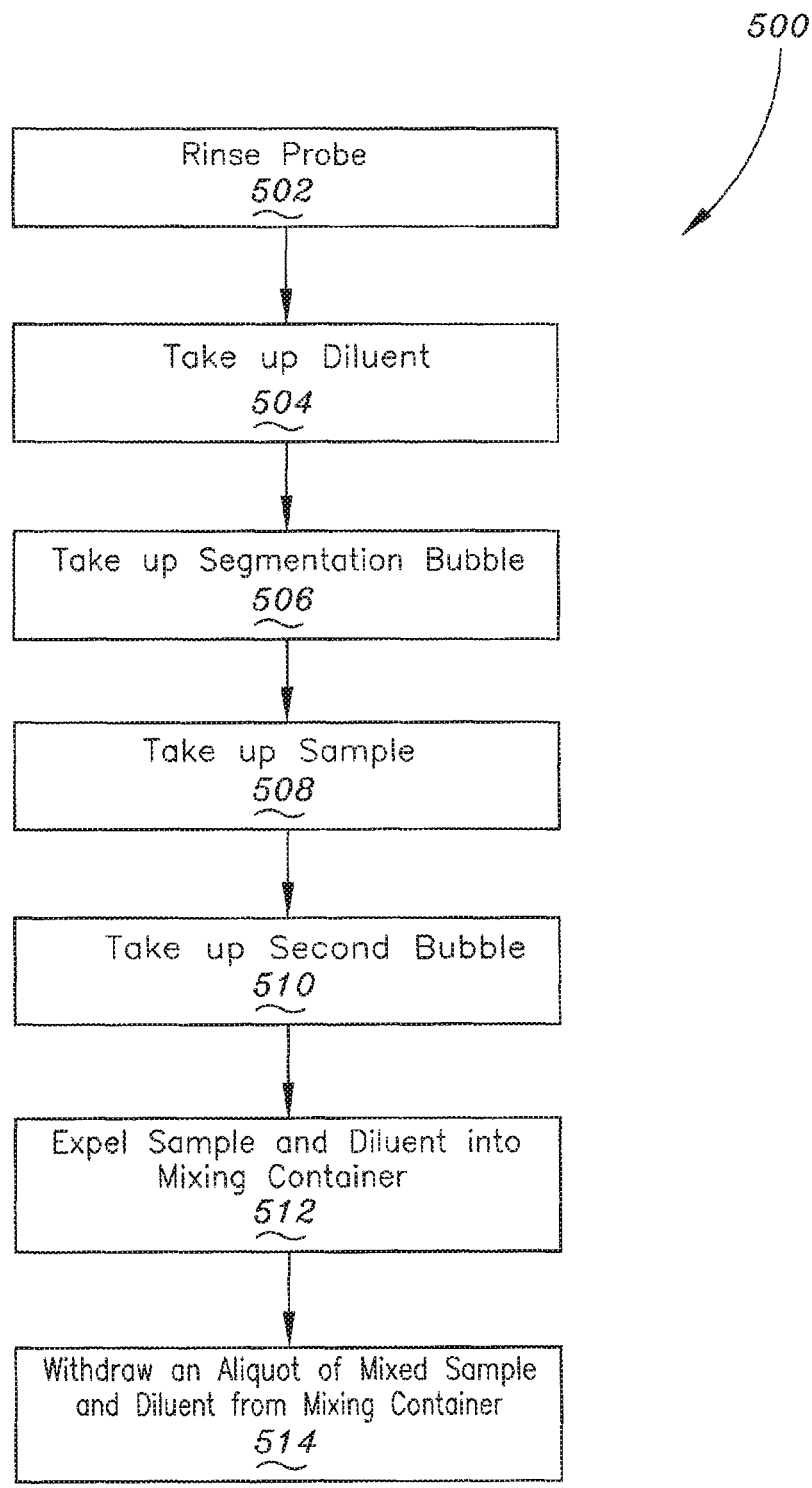
FIG. 5 is a flow diagram illustrating a procedure in an example implementation to add a diluent to a sample and insert the sample and diluent into a container.

Referring again to FIG. 5, an aliquot of the mixed sample and diluent is then withdrawn from the mixing container 106 (Block 514). For example, as shown in FIG. 1B, after expulsion of the sample and diluent, the first valve 118 is again actuated to its second state so that the first port 122 of the first valve 118 is connected with the second port 124 and the third port 126 is connected with the fourth port 128 to couple the sample loop 116 between the capillary 114 and line 156. The second valve 120 is also actuated to its second state so that the first port 134 of the second valve 120 is connected with the second port 136 to couple line 156 with line 166. In this manner, a vacuum is applied to the probe 104 to draw the mixed sample and diluent through the probe 104 and capillary 114 into the sample loop 116.

In some applications, expulsion of the sample and diluent from the probe 104 (Block 512) may sufficiently mix the sample and diluent to allow withdrawal of an aliquot of mixed sample and diluent. However, in other applications, additional mixing of the sample may be provided. In such applications, additional mixing may be provided via additional gas injection, for example, in accordance with aspects of the procedure 200 of FIG. 2.

In the discussion above, reference has been made to an example implementation in which the sample introduction system 102 is used in the analysis of oil samples. However, it is contemplated that the sample introduction system 102 is not limited to this implementation, but instead may be used in the analysis of a variety of sample substances. For example, in other implementations, the sample introduction system 102 may be used in the analysis of blood samples, wherein the diluent supplied is water or another suitable liquid.

CONCLUSION

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:
1. A method comprising:
causing a probe to be inserted into a supply of diluent;
causing diluent to be drawn from the supply of diluent into the probe;
causing the probe to be removed from the supply of diluent;
causing atmospheric gas to be drawn into the probe to form a segmentation bubble extending within the probe;
causing the probe to be inserted into a container containing a sample;
causing the sample to be drawn from the container containing the sample into the probe, the segmentation bubble being configured to separate the diluent from the sample;

causing the probe to be removed from the container containing the sample;

causing the probe to be inserted into a mixing container and the sample and the diluent to be subsequently expelled from the probe into the mixing container to mix the sample and the diluent;

causing gas to be injected into the mixing container through the probe to further mix the sample and the diluent within the mixing container; and causing an aliquot of the mixed sample and diluent to be withdrawn from the container.

2. The method as recited in claim 1, further comprising causing the probe to be inserted into a rinse station containing rinse fluid prior to causing the probe to be inserted into the supply of diluent, and causing the rinse fluid to be drawn from the rinse station containing the rinse fluid through the probe.

3. The method as recited in claim 2, further comprising causing a gas to be injected through the probe while the probe is rinsed at the rinse station.

4. The method as recited in claim 1, wherein causing the atmospheric gas to be drawn into the probe to form a segmentation bubble comprises causing the atmospheric gas to be drawn into the probe while the probe is moved from the supply of diluent to the container containing the sample.

5. The method as recited in claim 1, further comprising causing atmospheric gas to be drawn into the probe to form a second bubble extending within the probe prior to causing the sample and the diluent to be expelled from the probe into the mixing container to mix the sample and the diluent, the second bubble being configured to retard leakage of the sample from the probe.

6. A sample introduction system comprising:
a probe configured to be inserted into a supply of diluent and subsequently into a container containing a sample and subsequently into a mixing container; and
a pump and a valve assembly together being operable to cause diluent to be drawn into the probe, sample to be drawn into the probe, atmospheric gas to be drawn into the probe between the diluent and the sample, and the sample and the diluent to be expelled from the probe into the mixing container to mix the sample and the diluent, wherein the pump is configured to apply a vacuum to withdraw an aliquot of the mixed sample and diluent from the mixing container.

7. The sample introduction system as recited in claim 6, wherein the sample introduction system further includes an autosampler, the autosampler being configured to insert the probe into a rinse station containing rinse fluid prior to inserting the probe into the supply of diluent, and the pump being configured to apply a vacuum to draw a rinse fluid from the rinse station through the probe.

8. The sample introduction system as recited in claim 7, wherein the pump is configured to inject a gas through the probe while the probe is rinsed at the rinse station.

9. The sample introduction system as recited in claim 6, wherein the pump is configured to apply a vacuum to draw the atmospheric gas into the probe to form a segmentation bubble extending within the probe while the probe is moved from the supply of diluent to the container containing the sample, the segmentation bubble being configured to separate the diluent from the sample.

10. The sample introduction system as recited in claim 6, wherein the pump is configured to apply a vacuum to the probe to draw atmospheric gas into the probe to form a segmentation bubble extending within the probe after the sample is drawn into the probe and prior to expelling the sample and the diluent from the probe into the mixing container to mix the sample and the diluent.

11. The sample introduction system as recited in claim 6, wherein the pump is configured to apply a vacuum to the probe to draw atmospheric gas into the probe to form a segmentation bubble extending within the probe while the probe is moved from the container containing the sample to the mixing container.

12. The sample introduction system as recited in claim 6, wherein the pump is configured to apply a vacuum to the probe and withdraw an aliquot of the mixed sample and diluent from the mixing container.

13. A method comprising:
causing a probe to be inserted into a supply of diluent;
causing diluent to be drawn from the supply of diluent into the probe;
causing the probe to be removed from the supply of diluent;
causing atmospheric gas to be drawn into the probe to form a segmentation bubble extending within the probe;
causing the probe to be inserted into a container containing a sample;
causing the sample to be drawn from the container containing the sample into the probe, the segmentation bubble being configured to separate the diluent from the sample;
causing the probe to be removed from the container containing the sample;
causing the probe to be inserted into a mixing container and the sample and the diluent to be subsequently expelled from the probe into the mixing container to mix the sample and the diluent;
causing gas to be injected into the mixing container through the probe to further mix the sample and the diluent within the mixing container;
causing an aliquot of the mixed sample and diluent to be withdrawn from the container;
causing atmospheric gas to be drawn into the probe to form a second bubble extending within the probe prior to causing the sample and the diluent to be expelled from the probe into the mixing container to mix the sample and the diluent, the second bubble being configured to retard leakage of the sample from the probe, wherein causing the atmospheric gas to be drawn into the probe to form the second segmentation bubble comprises causing the atmospheric gas to be drawn into the probe while the probe is moved from the container containing the sample to the mixing container.

* * * * *